(12) United States Patent
Devi et al.

(10) Patent No.: US 10,635,492 B2
(45) Date of Patent: Apr. 28, 2020

(54) LEVERAGING SHARED WORK TO ENHANCE JOB PERFORMANCE ACROSS ANALYTICS PLATFORMS

(71) Applicant: International Business Machines Corporation, Armonk, NY (US)

(72) Inventors: Umamaheswari Devi, Bangalore (IN); Ravi Kothari, Bangalore (IN); Mudit Verma, New Delhi (IN)

(73) Assignee: International Business Machines Corporation, Armonk, NY (US)

( * ) Notice: Subject to any disclaimer, the term of this patent is extended or adjusted under 35 U.S.C. 154(b) by 194 days.

(21) Appl. No.: 15/295,432

(22) Filed: Oct. 17, 2016

(65) Prior Publication Data

US 2018/0107513 A1 Apr. 19, 2018

(51) Int. Cl.
*G06F 9/50* (2006.01)
*G16H 50/50* (2018.01)
*G06Q 10/06* (2012.01)

(52) U.S. Cl.
CPC ............... *G06F 9/50* (2013.01); *G06F 9/505* (2013.01); *G06Q 10/06311* (2013.01); *G16H 50/50* (2018.01)

(58) Field of Classification Search
CPC ..... G06F 9/50; G06F 9/505; G06Q 10/06311; G16H 50/50
See application file for complete search history.

(56) References Cited

U.S. PATENT DOCUMENTS

| | | | |
|---|---|---|---|
| 7,236,976 B2 | 6/2007 | Breitenbach et al. | |
| 9,183,058 B2 | 11/2015 | Li et al. | |
| 9,342,355 B2 | 5/2016 | Lin et al. | |
| 2005/0177824 A1* | 8/2005 | Kipman | G06F 8/71 717/162 |
| 2005/0256971 A1* | 11/2005 | Colrain | G06F 9/505 709/238 |

(Continued)

OTHER PUBLICATIONS

Yao et al., "LsPS: A Job Size-Based Scheduler for Efficient Task Assignments in Hadoop"—IEEE Transactions on Cloud Computing, vol. 3, No. 4, Oct.-Dec. 2015.
(Continued)

*Primary Examiner* — Meng Ai T An
*Assistant Examiner* — Michael W Ayers
(74) *Attorney, Agent, or Firm* — Ryan, Mason & Lewis, LLP

(57) ABSTRACT

Methods, systems, and computer program products for leveraging shared work to enhance job performance across analytics platforms are provided herein. A computer-implemented method includes comparing one or more task characteristics of multiple tasks across multiple jobs to be executed within a given environment, wherein each of the multiple jobs comprises one or more tasks; identifying, based on said comparing, one or more of the multiple tasks that can be shared by two or more of the multiple jobs; scheduling the multiple jobs for execution within the given environment, wherein said scheduling is based on (i) the identified tasks that can be shared by two or more of the multiple jobs, and (ii) one or more performance metrics of the given environment; and allocating resources to the multiple jobs based on said scheduling.

18 Claims, 5 Drawing Sheets

(56) References Cited

U.S. PATENT DOCUMENTS

| | | | |
|---|---|---|---|
| 2009/0320040 A1* | 12/2009 | Robison | G06F 9/5033 718/105 |
| 2012/0185859 A1* | 7/2012 | Kashiwaya | G06F 9/30076 718/100 |
| 2013/0104140 A1* | 4/2013 | Meng | G06F 9/4881 718/104 |
| 2013/0185722 A1* | 7/2013 | Kruglick | G06Q 10/063 718/1 |
| 2014/0137132 A1* | 5/2014 | Agarwal | G06F 9/5044 718/104 |
| 2015/0006234 A1 | 1/2015 | Boyette et al. | |
| 2015/0006735 A1* | 1/2015 | Chai | G06F 15/00 709/226 |
| 2015/0113540 A1* | 4/2015 | Rabinovici | G06F 9/5011 718/104 |
| 2015/0370589 A1* | 12/2015 | Bidarkar | G06F 9/45558 718/1 |

OTHER PUBLICATIONS

Popa et al., "DryadInc: Reusing work in large-scale computations," Workshop on Hot Topics in Cloud Computing 2009 (HotCloud 09).

Niu et al, "Employing Checkpoint to Improve Job Scheduling in Large-Scale Systems," Chapter Job Scheduling Strategies for Parallel Processing, vol. 7698 of the series Lecture Notes in Computer Science pp. 36-55, May 2012.

Curino et al. "Reservation-based Scheduling: If You're Late Don't Blame Us!" Microsoft Tech-Report: MSR-TR-2013-108, 2013.

Lei, et al, "Redoop: Supporting Recurring Queries in Hadoop," Proc. 17th International Conference on Extending Database Technology (EDBT), Mar. 24-28, 2014.

Peter Mell et al. The NIST Definition of Cloud Computing, Recommendations of the National Institute of Standards and Technology, U.S. Department of Commerce, Special Publication 800-145, Sep. 2011, 7 pages.

* cited by examiner

LEVERAGING SHARED WORK TO ENHANCE JOB PERFORMANCE ACROSS ANALYTICS PLATFORMS

FIELD

The present application generally relates to information technology, and, more particularly, to analytics platform management.

BACKGROUND

Large-scale analytics platforms can be expensive to build and maintain. As such, it is advantageous and often necessary to run such platforms at high rates of utilization. Also, such platforms are commonly required to run different kinds of jobs on a given cluster, wherein such jobs might include, for example, production jobs with deadlines, batch jobs, low latency, interactive jobs, service jobs, etc. Large-scale platforms are also commonly used by a large number of users, and such users often create significant overlapping computations among the submitted jobs, which can present opportunities that can be leveraged, for example, with respect to meeting service level agreement (SLA) obligations.

SUMMARY

In one embodiment of the present invention, techniques for leveraging shared work to enhance job performance across analytics platforms are provided. An exemplary computer-implemented method can include comparing one or more task characteristics of multiple tasks across multiple jobs to be executed within a given environment, wherein each of the multiple jobs comprises one or more tasks. Such a method can also include identifying, based on the comparing, one or more of the multiple tasks that can be shared by two or more of the multiple jobs, and scheduling the multiple jobs for execution within the given environment, wherein scheduling is based on (i) the identified tasks that can be shared by two or more of the multiple jobs, and (ii) one or more performance metrics of the given environment. Further, such a method can also include allocating resources to the multiple jobs based on the scheduling.

In another embodiment of the invention, an exemplary computer-implemented method can include generating a directed acyclic graph representation for each of multiple jobs to be executed within an analytics platform, wherein each node of the directed acyclic graph representations represents a task of the job. Such a method can also include creating a computation fingerprint for each node of the directed acyclic graph representations, wherein the computation fingerprint comprises (i) one or more input channels of the task, (ii) an identification of the environment of the task, (iii) one or more start-up arguments of the task, and (iv) the output produced by the task. Additionally, such a method can include identifying one or more nodes across the directed acyclic graph representations that share identical computation fingerprints, wherein the identified nodes represent tasks that can be shared by the jobs represented by the respective directed acyclic graph representations. Further, such a method can also include scheduling the multiple jobs for execution within the analytics platform, wherein scheduling is based on (i) the identified nodes, and (ii) one or more performance metrics of the analytics platform, and allocating resources to the multiple jobs based on the scheduling.

Another embodiment of the invention or elements thereof can be implemented in the form of a computer program product tangibly embodying computer readable instructions which, when implemented, cause a computer to carry out a plurality of method steps, as described herein. Furthermore, another embodiment of the invention or elements thereof can be implemented in the form of a system including a memory and at least one processor that is coupled to the memory and configured to perform noted method steps. Yet further, another embodiment of the invention or elements thereof can be implemented in the form of means for carrying out the method steps described herein, or elements thereof; the means can include hardware module(s) or a combination of hardware and software modules, wherein the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION

Figure 1:
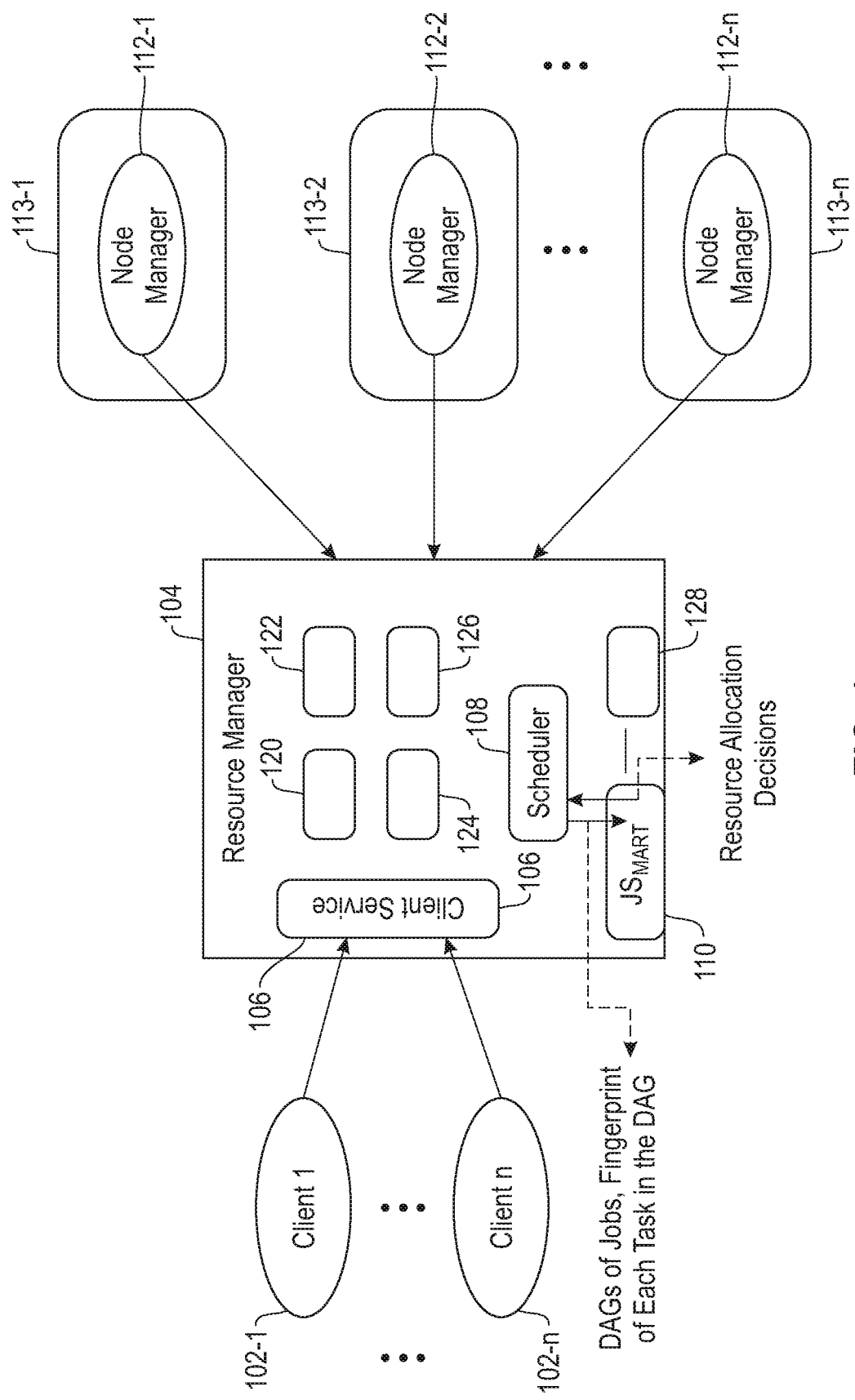
FIG. 1 is a diagram illustrating system architecture, according to an exemplary embodiment of the invention.

As described herein, an embodiment of the present invention includes leveraging shared work to enhance job performance across large-scale analytics platforms. At least one embodiment of the invention can include scheduling multiple workflows within an analytics platform, taking into account one or more identified shared computations with outputs that can be reused across workflows. As detailed herein, such sharing of computation tasks across workflows and/or jobs can result in reducing job response times as well as optimizing overall throughput of the platform.

One or more embodiments of the invention can include identifying common, shared, and/or re-usable computing sub-tasks across different jobs and/or tasks executing within a platform. Additionally, such an embodiment can include scheduling multiple jobs, and assigning resources to those multiple jobs, taking into account the identified common, shared, and/or re-usable computing sub-tasks to reduce the overall waiting time for the platform/system, as well as to maximize system fairness across jobs. As is generally understood, a fair scheduler commonly distributes the resources of a system equally among jobs. When jobs share tasks, such jobs may receive fewer resources. That said, one or more embodiments of the invention can include techniques for ameliorating such unfairness. Further, in one or more embodiments of the invention, such multiple jobs can include batch jobs (with deadlines) and/or interactive jobs.

By way merely of illustration, consider a healthcare analytics example within the context of a healthcare analytics system for building predictive models for various target conditions. Different users (for example, doctors) may be utilizing the analytics system to model the progression of different diseases, or to use data from various, but overlapping, time periods. Common and/or shared sub-tasks within different jobs executing on the model (for instance, jobs pertaining to diverse target conditions) can be identified by at least one embodiment of the invention. Taking such shared computations into consideration while scheduling jobs can lead to improved system performance.

By way of more specific example, a healthcare modeling pipeline can include a sequence of tasks comprising (i) cohort construction, (ii) feature construction, (iii) cross validation, (iv) feature selection, and (v) classification. In such a pipeline, the tasks specified are executed in the specified sequence, with the output of a preceding task providing all or part of the input to the task following it in the pipeline. The input to the first task can be derived from one or more external sources. Such modeling pipelines for various conditions can overlap to varying extents. For example, predicting heart disease and diabetes can include common cohort aspects. As used in this specific example, a cohort refers to a set of people whose health parameters are used in developing a model that can be used to predict the onset or progression of a disease. For instance, people with neither diabetes nor heart disease can be a common sub-cohort for models for these two diseases. Accordingly, cohort construction and feature construction for the common sub-cohorts will be common and can be used across both jobs and/or workflows.

Similar opportunities for reusing computation components and/or sub-tasks exist in other analytics systems, such as weather modeling and prediction systems, sales prediction systems, market forecast systems, etc. By way of further example, in a natural language processing system (such as question answering system), multiple common sub-tasks, such as constructing word vectors from a common set of documents, are often present. Additionally, in medical image processing systems, different types of diagnostic tasks often require common operations such as segmentation, filtering, etc.

FIG. 1 is a diagram illustrating system architecture, according to an embodiment of the invention. The system includes computing nodes, 113-1, 113-2, . . . 113-$n$ (collectively referred to herein as computing nodes 113), on which node managers 112-1, 112-2, . . . 112-$n$ (collectively referred to herein as node managers 112), respectively, are executing. The computing nodes 113 can include distinct physical nodes and/or logical nodes. Further, one or more jobs can be executed on the computing nodes 113. The node managers 112 are responsible for allocating needed resources for those jobs on the computing nodes 113.

Also, FIG. 1 depicts clients 102-1 through 102-$n$ (collectively referred to herein as clients 102), and a resource manager system 104. The resource manager system 104 receives requests for job execution from clients 102 and is responsible for arbitrating resources available on the computing nodes 113 among the submitted jobs. Accordingly, the resource manager system 104 includes a client service component 106, which receives requests for job execution from clients 102. In other words, the clients 102 submit jobs for execution to the system 104 using the client service component 106.

The client service component 106 is also responsible for informing clients 102 when their jobs complete execution or encounter failures. The component 106 also responds to client queries enquiring about the status of submitted jobs. Additionally, to help with resource distribution among jobs, the resource manager system 104 includes a scheduler component 108 and a component for optimizing a system performance metric 110, such as, an average response time minimization component ($JS_{MART}$).

As also illustrated in FIG. 1, the resource manager system 104 can include one or more other components such as a job manager 120 for maintaining the status of jobs submitted to the system, a security management component 122, a job master service 124 for allocating resources for jobs on computing nodes 113, a resource tracker 126 that maintains the state of the computing nodes 113, and an administrator service 128 to respond to overall system health related queries.

Additionally, the scheduler component 108 provides input to the system metric optimization component 110, wherein such input can include one or more directed acyclic graphs (DAGs) of client jobs, as well as the computation fingerprint (as further described herein) of each task of the DAGs. Also, the average response time minimization component 110, based on such input, generates resource allocation decisions with respect to the client jobs, and provides such decisions to the scheduler component 108. Further, the output of the scheduler component 108 can be used by the job master component 124 of the resource manager 104 to negotiate with the node managers 112 running on the computing nodes 113 to allocate resources for the jobs in accordance with the specifications received from the scheduler component 108.

As detailed herein, at least one embodiment of the invention includes identifying shared and/or reusable computations across distinct jobs executing within an analytics platform. In such an embodiment, shared and/or reusable computation can be identified using computation fingerprints associated with each executable (task, sub-task, etc.). As used herein, a computation fingerprint includes information on the executable such as input channels (for example, files, blocks, partitions, and/or output(s) of a process) of the executable, environment of the executable, start-up arguments, and output produced. In one or more embodiments of the invention, two computations are re-usable (for one another) if their fingerprints match.

As also detailed herein, a job model can include a DAG representation, wherein each node represents some computation and/or process (also referred to herein as a task), and wherein each node (task) has a corresponding computation fingerprint. Additionally, jobs within an analytics platform/system can share tasks to varying extents.

At least one embodiment of the invention can also include prioritizing the sharing and/or re-use of one or more tasks within a system. By way of illustration, in leveraging knowledge of shared tasks to enhance a system performance metric, assume that average job response time is the given system performance metric. Shortest Job First (SJF), for example, can be implemented to minimize the average response time for the system if jobs do not have shared tasks. In SJF, a job with the shortest execution time is prioritized over the other jobs. When jobs share tasks, the execution time of the shared tasks can be attributed equally to all of its jobs by distributing the execution time equally among all such jobs. Thus, the effective execution requirement of a long job can be lower than that of a short job, if the long job has more shared tasks than the short one. Hence, tasks can be prioritized based on sharing and/or re-use across multiple jobs, as well as the effective job execution times associated with each sharing and/or re-use configuration.

Additionally, in one or more embodiments of the invention, when a task common to a sub-group executes, the cumulative resource will be allocated to the executing task. Further, in connection with minimizing average response time ($JS_{MART}$), when jobs share tasks, executing a long(er)

job that shares tasks with other (shorter) jobs first can sometimes reduce the completion times of all of the sharing jobs. Accordingly, the average job response time can be reduced.

At least one embodiment of the invention can also include implementing one or more data structures. Such data structures can include, for example, a priority queue (Task_Q) of all tasks that have not yet been executed by the analytics platform/system. Each node in the queue is labelled by the corresponding task computation fingerprint and contains a [job list, average job execution cost] label, wherein a job list refers to the list of all jobs of which the task is a part, and average job execution cost refers to the average execution time of all jobs in the job list, assuming each shared task is executed only once. Another data structure can include a hash map (T2J_Map) from a task computation fingerprint, to a pointer to a corresponding node in the priority queue (Task_Q). When a new job is submitted, T2J_Map is used to identify all of the tasks of the job that are shared. Further, yet another data structure can include a hash map (J2T_Map) from a job identifier (ID) to a list of all task fingerprints associated with that job ID.

Also, in connection with minimizing average response time, one or more embodiments of the invention include a job submission aspect and a job selection aspect. Accordingly, for each job (J) that is submitted, at least one embodiment of the invention includes constructing a hash map (J2T_Map). For each task (T) of the newly-submitted job (J), if a task fingerprint exists, at least one embodiment of the invention includes identifying the job list (within the relevant priority queue (Task_Q)) in the node for task (T), whose average execution cost (i) would be the least if the current job is added thereto and (ii) is lower than the incoming job's (J's) execution cost.

If such a job list is found for task T, job J is inserted in that job list for task T in the priority queue (Task_Q). Otherwise, at least one embodiment of the invention includes creating a new [job list, average job execution cost] label with the current job and its execution cost, and adding the label to the task. Additionally, such an embodiment can include updating task T's execution cost to the lowest of any of its job lists' execution costs, and correspondingly adjusting the priority queue (Task_Q, so that it remains a priority queue). Otherwise, one or more embodiments of the invention can include inserting the task fingerprint in the hash map (T2J_Map), as well as creating and adding a [job list, average job execution cost] label containing only the current job in the job list and its execution cost.

Further, when a new job needs to be selected for execution (that is, when resources become and/or are still available), at least one embodiment of the invention can include the following sequence of steps. Let a candidate job (cand_job) =the job with the minimum execution cost in the job list with the lowest average execution cost in the head node of a priority queue (Task_Q). Accordingly, one or more embodiments of the invention can include scheduling cand_job for execution. For each task of cand_job that completes execution or is preempted, such an embodiment can include adjusting the node corresponding to the task in the priority queue (Task_Q) as follows: (i) Remove job J from the node's job list; (ii) Lower the average execution cost of the remaining jobs, accounting for all of their tasks that completed execution as part of cand_job; and (iii) Adjust the priority queue (Task_Q). For the tasks of cand_job that are only partially executed, the remaining execution cost can be updated.

As also detailed herein, one or more embodiments of the invention can include enhancing the fairness of a fair scheduler. In such an embodiment, for each job, one of the eligible tasks for execution is selected. If m jobs have one common task executing, then such an embodiment includes allocating $(m/n) \times R$ of the R total resources to that common task. Here, n denotes the number of pending jobs (that is, jobs that have not completed execution) in the system. Additionally, the remaining resources can be allocated to the remaining jobs, taking their common tasks in execution into account.

Further, at least one embodiment of the invention includes scheduling mixed jobs. Some jobs, such as production jobs or service jobs, are associated with deadlines, while interactive jobs can require a low latency. As such, one or more embodiments of the invention can include determining the placement, in time and space, of production jobs based on their corresponding deadlines. Of tasks with equal priority within a job, such an embodiment can include prioritizing chains of tasks that are part of interactive, low-latency jobs. Further, such an embodiment of the invention can also include scheduling low-latency jobs using minimizing average response time ($J_{SMART}$) techniques.

Figure 2:
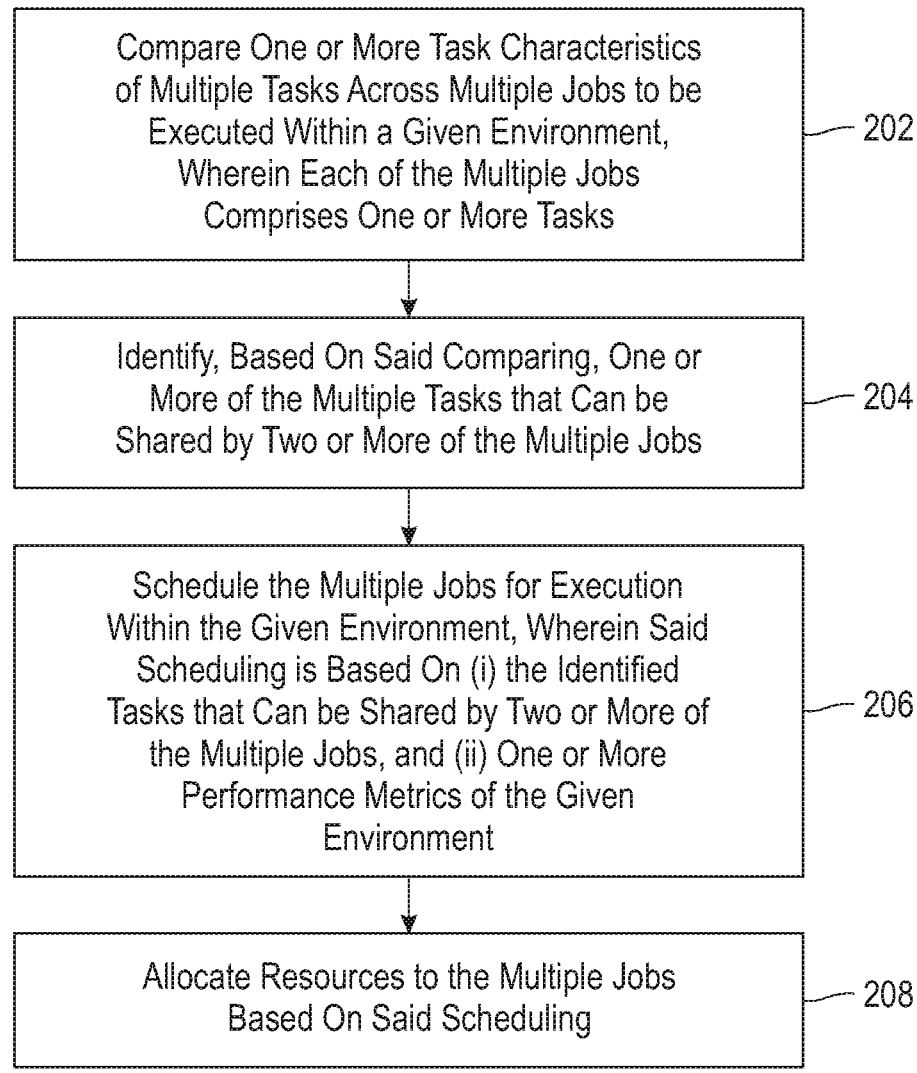
FIG. 2 is a flow diagram illustrating techniques according to an embodiment of the invention.

FIG. 2 is a flow diagram illustrating techniques according to an embodiment of the present invention. Step 202 includes comparing one or more task characteristics of multiple tasks across multiple jobs to be executed within a given environment, wherein each of the multiple jobs comprises one or more tasks. The given environment can include an analytics platform. The multiple jobs can include multiple batch jobs, multiple interactive jobs, or a combination of one or more batch jobs and one or more interactive jobs. Additionally, the task characteristics can include one or more input channels of the task, an environment of the task, one or more start-up arguments of the task, and/or an output produced by the task.

Step 204 includes identifying, based on said comparing, one or more of the multiple tasks that can be shared by two or more of the multiple jobs. Identifying can include identifying instances of a task in two or more of the jobs, wherein the instances can include identical values for the one or more task characteristics.

Step 206 includes scheduling the multiple jobs for execution within the given environment, wherein said scheduling is based on (i) the identified tasks that can be shared by two or more of the multiple jobs, and (ii) one or more performance metrics of the given environment. The performance metrics can include average job response time, and/or scheduling fairness. Additionally, scheduling can be further based on the job type of each of the multiple jobs.

Step 208 includes allocating resources to the multiple jobs based on said scheduling. Allocating can include prioritizing allocation of resources to jobs that share one or more tasks.

Also, an additional embodiment of the invention includes generating a directed acyclic graph representation for each of multiple jobs to be executed within an analytics platform, wherein each node of the directed acyclic graph representations represents a task of the job. Such an embodiment can also include creating a computation fingerprint for each node of the directed acyclic graph representations, wherein the computation fingerprint comprises (i) one or more input channels of the task, (ii) an identification of the environment of the task, (iii) one or more start-up arguments of the task, and (iv) the output produced by the task. Additionally, such an embodiment can include identifying one or more nodes across the directed acyclic graph representations that share identical computation fingerprints, wherein the identified nodes represent tasks that can be shared by the jobs represented by the respective directed acyclic graph representations. Further, such an embodiment can also include scheduling the multiple jobs for execution within the analytics platform, wherein scheduling is based on (i) the identified nodes, and (ii) one or more performance metrics of the analytics platform, and allocating resources to the multiple jobs based on the scheduling.

The techniques depicted in FIG. 2 can also, as described herein, include providing a system, wherein the system includes distinct software modules, each of the distinct software modules being embodied on a tangible computer-readable recordable storage medium. All of the modules (or any subset thereof) can be on the same medium, or each can be on a different medium, for example. The modules can include any or all of the components shown in the figures and/or described herein. In an embodiment of the invention, the modules can run, for example, on a hardware processor. The method steps can then be carried out using the distinct software modules of the system, as described above, executing on a hardware processor. Further, a computer program product can include a tangible computer-readable recordable storage medium with code adapted to be executed to carry out at least one method step described herein, including the provision of the system with the distinct software modules.

Additionally, the techniques depicted in FIG. 2 can be implemented via a computer program product that can include computer useable program code that is stored in a computer readable storage medium in a data processing system, and wherein the computer useable program code was downloaded over a network from a remote data processing system. Also, in an embodiment of the invention, the computer program product can include computer useable program code that is stored in a computer readable storage medium in a server data processing system, and wherein the computer useable program code is downloaded over a network to a remote data processing system for use in a computer readable storage medium with the remote system.

An embodiment of the invention or elements thereof can be implemented in the form of an apparatus including a memory and at least one processor that is coupled to the memory and configured to perform exemplary method steps.

Figure 3:
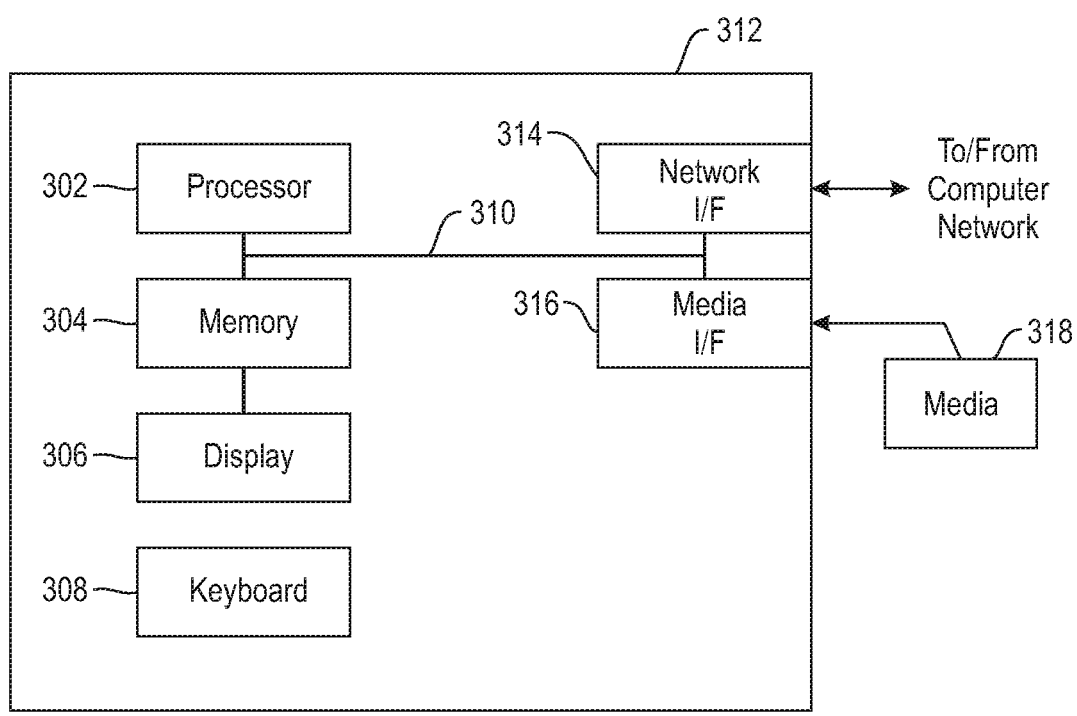
FIG. 3 is a system diagram of an exemplary computer system on which at least one embodiment of the invention can be implemented.

Additionally, an embodiment of the present invention can make use of software running on a computer or workstation. With reference to FIG. 3, such an implementation might employ, for example, a processor 302, a memory 304, and an input/output interface formed, for example, by a display 306 and a keyboard 308. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, a mechanism for inputting data to the processing unit (for example, mouse), and a mechanism for providing results associated with the processing unit (for example, printer). The processor 302, memory 304, and input/output interface such as display 306 and keyboard 308 can be interconnected, for example, via bus 310 as part of a data processing unit 312. Suitable interconnections, for example via bus 310, can also be provided to a network interface 314, such as a network card, which can be provided to interface with a computer network, and to a media interface 316, such as a diskette or CD-ROM drive, which can be provided to interface with media 318.

Accordingly, computer software including instructions or code for performing the methodologies of the invention, as described herein, may be stored in associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 302 coupled directly or indirectly to memory elements 304 through a system bus 310. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including, but not limited to, keyboards 308, displays 306, pointing devices, and the like) can be coupled to the system either directly (such as via bus 310) or through intervening I/O controllers (omitted for clarity).

Network adapters such as network interface 314 may also be coupled to the system to enable the data processing system to become coupled to other data processing systems or remote printers or storage devices through intervening private or public networks. Modems, cable modems and Ethernet cards are just a few of the currently available types of network adapters.

As used herein, including the claims, a "serve" includes a physical data processing system (for example, system 312 as shown in FIG. 3) running a server program. It will be understood that such a physical server may or may not include a display and keyboard.

The present invention may be a system, a method, and/or a computer program product at any possible technical detail level of integration. The computer program product may include a computer readable storage medium (or media) having computer readable program instructions thereon for causing a processor to carry out embodiments of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform embodiments of the present invention.

Embodiments of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be noted that any of the methods described herein can include an additional step of providing a system comprising distinct software modules embodied on a computer readable storage medium; the modules can include, for example, any or all of the components detailed herein. The method steps can then be carried out using the distinct software modules and/or sub-modules of the system, as described above, executing on a hardware processor 302. Further, a computer program product can include a computer-readable storage medium with code adapted to be implemented to carry out at least one method step described herein, including the provision of the system with the distinct software modules.

In any case, it should be understood that the components illustrated herein may be implemented in various forms of hardware, software, or combinations thereof, for example, application specific integrated circuit(s) (ASICS), functional circuitry, an appropriately programmed digital computer with associated memory, and the like. Given the teachings of the invention provided herein, one of ordinary skill in the related art will be able to contemplate other implementations of the components of the invention.

Additionally, it is understood in advance that implementation of the teachings recited herein are not limited to a particular computing environment. Rather, embodiments of the present invention are capable of being implemented in conjunction with any type of computing environment now known or later developed.

For example, cloud computing is a model of service delivery for enabling convenient, on-demand network access to a shared pool of configurable computing resources (for example, networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (for example, country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (for example, storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (for example, web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (for example, host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (for example, mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (for example, cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
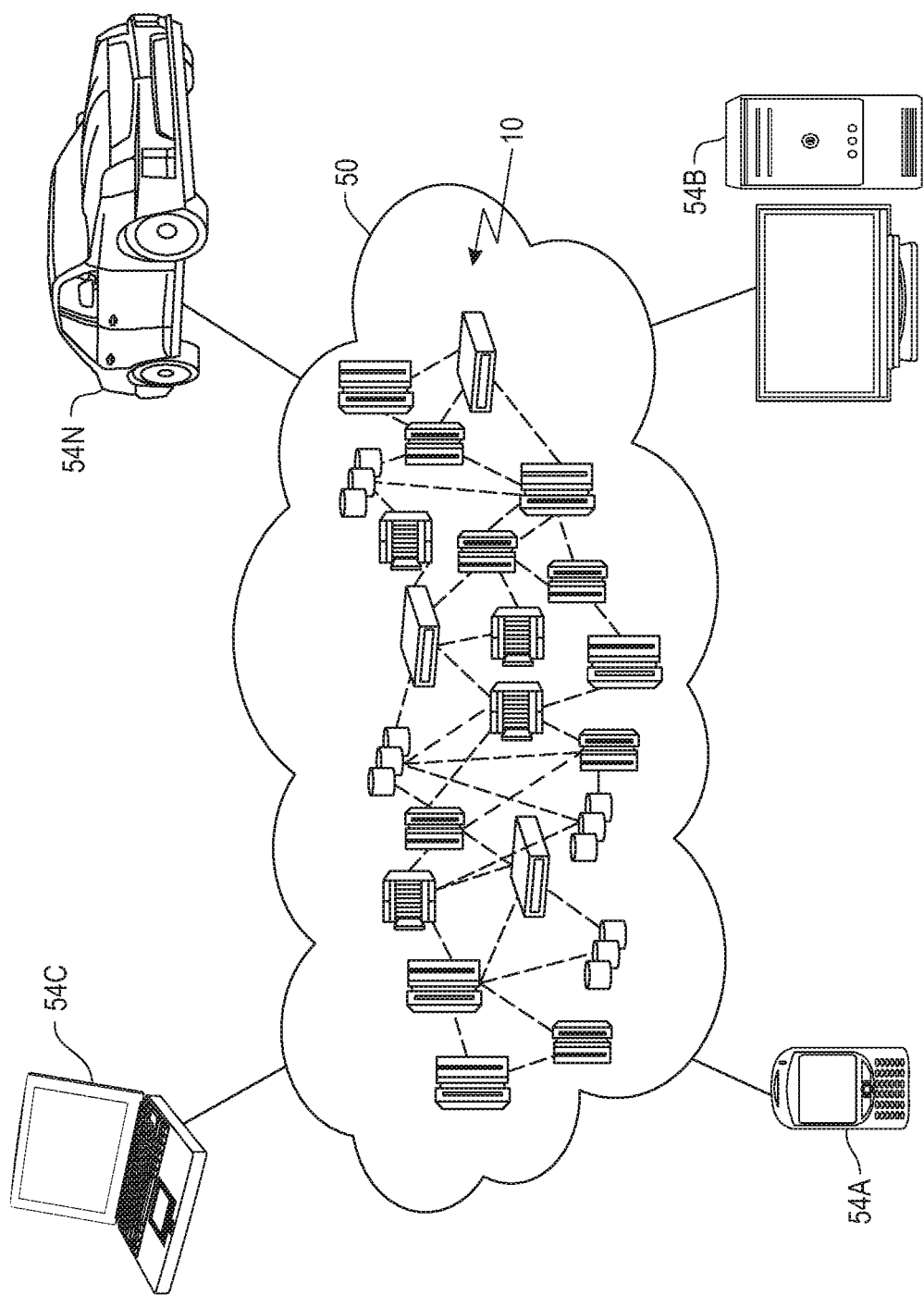
FIG. 4 depicts a cloud computing environment according to an embodiment of the present invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
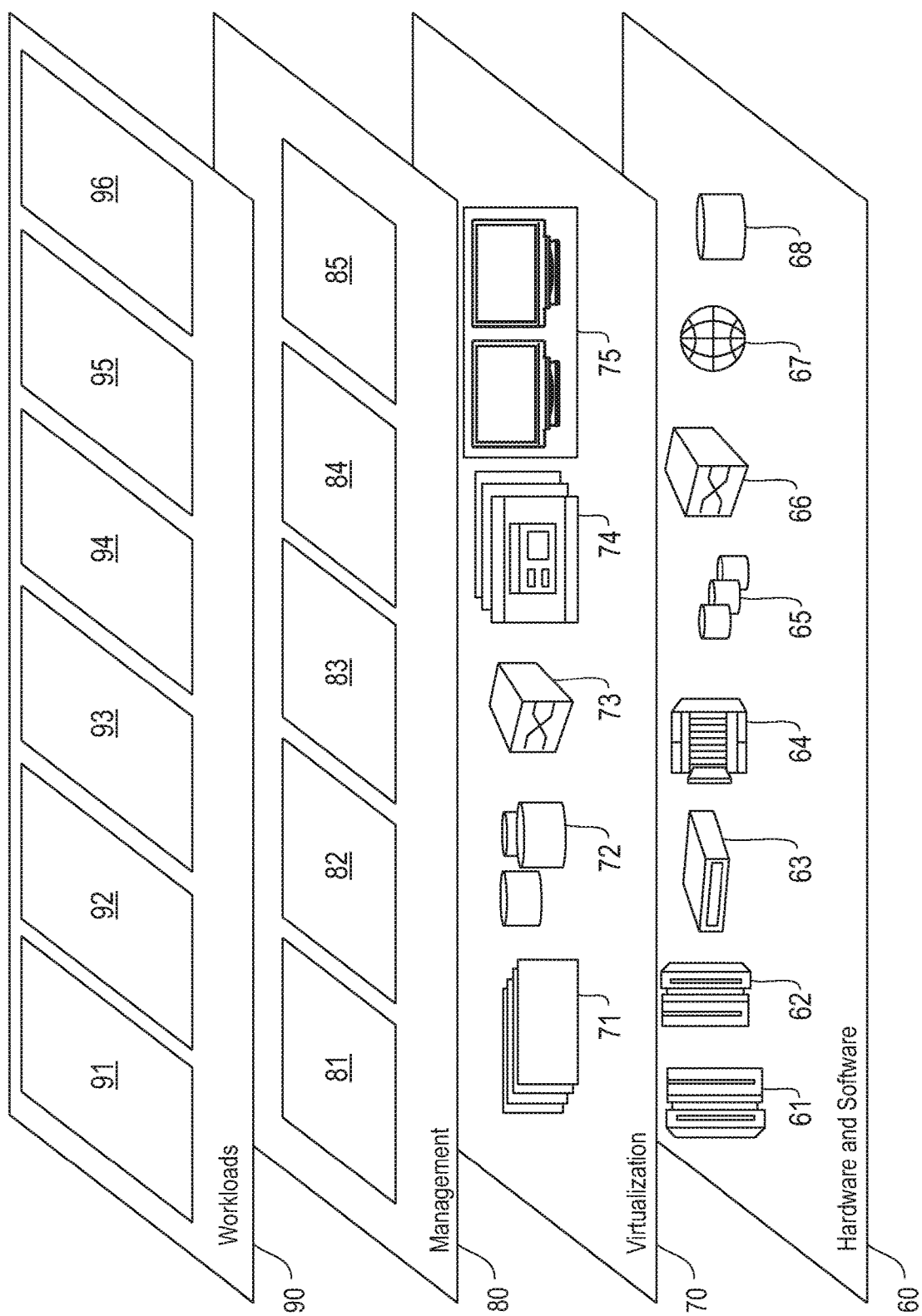
FIG. 5 depicts abstraction model layers according to an embodiment of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75. In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources.

In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and job-related resource allocation 96, in accordance with the one or more embodiments of the present invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, sharing of computation tasks across workflows and/or jobs to reduce job response times and optimize overall throughput of an analytics platform.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
    comparing one or more task characteristics of each of multiple tasks across multiple jobs to be executed within a given environment, wherein each of the multiple jobs comprises one or more tasks;
    identifying, based on said comparing, one or more of the multiple tasks that can be shared by two or more of the multiple jobs;
    generating and implementing a plurality of data structures, wherein the plurality of data structures comprise:
        (i) a data structure containing a priority queue comprising multiple nodes each corresponding to, and identifying each of the multiple tasks that has not yet been executed within the given environment, wherein each node in the priority queue is labelled via (a) a job list label and (b) an average job execution cost label, wherein the job list label refers to a list of each of the multiple jobs to which the task is a part, and wherein the average job execution cost label refers to an average execution time of each of the multiple jobs in the list, assuming each shared task is executed only once;
        (ii) a data structure containing a first hash map that maps a task computation fingerprint for each of the multiple tasks to a pointer to a corresponding node in the priority queue; and
        (iii) a data structure containing a second hash map that maps a job identifier each of the multiple jobs to a list of all task computation fingerprints associated with that job identifier;
    scheduling the multiple jobs for execution within the given environment, wherein said scheduling is based on (i) the identified tasks that can be shared by two or more of the multiple jobs, (ii) utilization of the plurality of data structures, and (iii) one or more performance metrics of the given environment, and wherein said scheduling comprises planning (a) execution of a first of the two or more jobs having one or more of the multiple tasks that can be shared and (b) reuse of one or more outputs, attributed to the one or more tasks that can be shared, from the job planned for execution in the remaining one or more jobs that share the one or more tasks, wherein the one or more performance metrics comprises average job response time, wherein for the two or more jobs that have one or more of the multiple tasks that can be shared, execution time of each of the one or more tasks that can be shared is attributed proportionately to all of the jobs that can share the task by equally proportioning the execution time across all of the jobs that can share the task; and
    allocating resources to the multiple jobs based on said scheduling;
    wherein the method is carried out by at least one computing device.

2. The computer-implemented method of claim 1, wherein the multiple jobs comprise multiple batch jobs.

3. The computer-implemented method of claim 1, wherein the multiple jobs comprise multiple interactive jobs.

4. The computer-implemented method of claim 1, wherein the multiple jobs comprise one or more batch jobs and one or more interactive jobs.

5. The computer-implemented method of claim 1, wherein the one or more task characteristics comprises one or more input channels.

6. The computer-implemented method of claim 1, wherein the one or more task characteristics comprises one or more start-up arguments.

7. The computer-implemented method of claim 1, wherein the one or more task characteristics comprises an output.

8. The computer-implemented method of claim 1, wherein said identifying comprises identifying instances of the same task in two or more of the jobs, wherein the instances comprise identical values for the one or more task characteristics.

9. The computer-implemented method of claim 1, wherein the one or more performance metrics comprises scheduling fairness.

10. The computer-implemented method of claim 1, wherein said scheduling is further based on the job type of each of the multiple jobs.

11. The computer-implemented method of claim 1, wherein said allocating comprises prioritizing allocation of resources to jobs that share one or more tasks.

12. The computer-implemented method of claim 1, wherein the given environment comprises an analytics platform.

13. A computer program product comprising a computer readable storage medium having program instructions embodied therewith, the program instructions executable by a device to cause the device to:
   compare one or more task characteristics of each of multiple tasks across multiple jobs to be executed within a given environment, wherein each of the multiple jobs comprises one or more tasks;
   identify, based on said comparing, one or more of the multiple tasks that can be shared by two or more of the multiple jobs;
   generate and implement a plurality of data structures, wherein the plurality of data structures comprise:
      (i) a data structure containing a priority queue comprising multiple nodes each corresponding to, and identifying each of the multiple tasks that has not yet been executed within the given environment, wherein each node in the priority queue is labelled via (a) a job list label and (b) an average job execution cost label, wherein the job list label refers to a list of each of the multiple jobs to which the task is a part, and wherein the average job execution cost label refers to an average execution time of each of the multiple jobs in the list, assuming each shared task is executed only once;
      (ii) a data structure containing a first hash map that maps a task computation fingerprint for each of the multiple tasks to a pointer to a corresponding node in the priority queue; and
      (iii) a data structure containing a second hash map that maps a job identifier each of the multiple jobs to a list of all task computation fingerprints associated with that job identifier;
   schedule the multiple jobs for execution within the given environment, wherein said scheduling is based on (i) the identified tasks that can be shared by two or more of the multiple jobs, (ii) utilization of the plurality of data structures, and (iii) one or more performance metrics of the given environment, and wherein said scheduling comprises planning (a) execution of a first of the two or more jobs having one or more of the multiple tasks that can be shared and (b) reuse of one or more outputs, attributed to the one or more tasks that can be shared, from the job planned for execution in the remaining one or more jobs that share the one or more tasks, wherein the one or more performance metrics comprises average job response time, wherein for the two or more jobs that have one or more of the multiple tasks that can be shared, execution time of each of the one or more tasks that can be shared is attributed proportionately to all of the jobs that can share the task by equally proportioning the execution time across all of the jobs that can share the task; and
   allocate resources to the multiple jobs based on said scheduling.

14. The computer program product of claim 13, wherein said identifying comprises identifying instances of a task in two or more of the jobs, wherein the instances comprise identical values for the one or more task characteristics.

15. The computer program product of claim 13, wherein said scheduling is further based on the job type of each of the multiple jobs.

16. The computer program product of claim 13, wherein said allocating comprises prioritizing allocation of resources to jobs that share one or more tasks.

17. A system comprising:
   a memory; and
   at least one processor coupled to the memory and configured for:
      comparing one or more task characteristics of each of multiple tasks across multiple jobs to be executed within a given environment, wherein each of the multiple jobs comprises one or more tasks;
      identifying, based on said comparing, one or more of the multiple tasks that can be shared by two or more of the multiple jobs;
      generating and implementing a plurality of data structures, wherein the plurality of data structures comprise:
         (i) a data structure containing a priority queue comprising multiple nodes each corresponding to, and identifying each of the multiple tasks that has not yet been executed within the given environment, wherein each node in the priority queue is labelled via (a) a job list label and (b) an average job execution cost label, wherein the job list label refers to a list of each of the multiple jobs to which the task is a part, and wherein the average job execution cost label refers to an average execution time of each of the multiple jobs in the list, assuming each shared task is executed only once;
         (ii) a data structure containing a first hash map that maps a task computation fingerprint for each of the multiple tasks to a pointer to a corresponding node in the priority queue; and
         (iii) a data structure containing a second hash map that maps a job identifier each of the multiple jobs to a list of all task computation fingerprints associated with that job identifier;
      scheduling the multiple jobs for execution within the given environment, wherein said scheduling is based on (i) the identified tasks that can be shared by two or more of the multiple jobs, (ii) utilization of the plurality of data structures, and (iii) one or more performance metrics of the given environment, and wherein said scheduling comprises planning (a) execution of a first of the two or more jobs having one or more of the multiple tasks that can be shared and (b) reuse of one or more outputs, attributed to the one or more tasks that can be shared, from the job planned for execution in the remaining one or more jobs that share the one or more tasks, wherein the one or more performance metrics comprises average job response time, wherein for the two or more jobs that have one or more of the multiple tasks that can be shared, execution time of each of the one or more tasks that can be shared is attributed proportionately to all of the jobs that can share the task by equally proportioning the execution time across all of the jobs that can share the task; and
      allocating resources to the multiple jobs based on said scheduling.

18. A computer-implemented method, comprising:

generating a directed acyclic graph representation for each of multiple jobs to be executed within an analytics platform, wherein each node of the directed acyclic graph representations represents a task of the job;

creating a computation fingerprint for each node of the directed acyclic graph representations, wherein the computation fingerprint comprises (i) one or more input channels of the task, (ii) one or more start-up arguments of the task, and (iii) the output produced by the task;

identifying nodes across the directed acyclic graph representations that share identical computation fingerprints, wherein the identified nodes represent tasks that can be shared by the jobs represented by the respective directed acyclic graph representations;

generating and implementing a plurality of data structures, wherein the plurality of data structures comprise:

(i) a data structure containing a priority queue comprising multiple nodes each corresponding to, and identifying each of the multiple tasks that has not yet been executed within the given environment, wherein each node in the priority queue is labelled via (a) a job list label and (b) an average job execution cost label, wherein the job list label refers to a list of each of the multiple jobs to which the task is a part, and wherein the average job execution cost label refers to an average execution time of each of the multiple jobs in the list, assuming each shared task is executed only once;

(ii) a data structure containing a first hash map that maps a task computation fingerprint for each of the multiple tasks to a pointer to a corresponding node in the priority queue; and (iii) a data structure containing a second hash map that maps a job identifier each of the multiple jobs to a list of all task computation fingerprints associated with that job identifier:

scheduling the multiple jobs for execution within the analytics platform, wherein said scheduling is based on (i) the identified nodes, (ii) utilization of the plurality of data structures, and (iii) one or more performance metrics of the analytics platform, and wherein said scheduling comprises planning (a) execution of a first of the two or more jobs having one or more of the multiple tasks that can be shared and (b) reuse of one or more outputs, attributed to the one or more tasks that can be shared, from the job planned for execution in the remaining one or more jobs that share the one or more tasks, wherein the one or more performance metrics comprises average job response time, wherein for the jobs that have one or more of the tasks that can be shared, execution time of each of the one or more tasks that can be shared is attributed proportionately to all of the jobs that can share the task by equally proportioning the execution time equally across all of the jobs that can share the task; and allocating resources to the multiple jobs based on said scheduling;

wherein the method is carried out by at least one computing device.

* * * * *